US012805971B2

(12) United States Patent
Keiper et al.

(10) Patent No.: US 12,805,971 B2
(45) Date of Patent: Nov. 24, 2026

(54) BREAST BIOPSY MARKER AND SYSTEM

(71) Applicant: Bard Peripheral Vascular, Inc., Franklin Lakes, NJ (US)

(72) Inventors: Nicholas Keiper, Tempe, AZ (US); Kyra Temple, Mesa, AZ (US); Zachary Willis, Mesa, AZ (US)

(73) Assignee: Bard Peripheral Vascular, Inc., Franklin Lakes, NJ (US)

( * ) Notice: Subject to any disclaimer, the term of this patent is extended or adjusted under 35 U.S.C. 154(b) by 310 days.

(21) Appl. No.: 18/001,781

(22) PCT Filed: Jun. 24, 2020

(86) PCT No.: PCT/US2020/039300
§ 371 (c)(1),
(2) Date: Dec. 14, 2022

(87) PCT Pub. No.: WO2021/262157
PCT Pub. Date: Dec. 30, 2021

(65) Prior Publication Data
US 2023/0255720 A1 Aug. 17, 2023

(51) Int. Cl.
*A61M 25/10* (2013.01)
*A61B 90/00* (2016.01)
*A61B 10/00* (2006.01)

(52) U.S. Cl.
CPC .......... *A61B 90/39* (2016.02); *A61B 10/0041* (2013.01); *A61B 2090/3908* (2016.02); (Continued)

(58) Field of Classification Search
CPC ............ A61B 90/39; A61B 2090/3908; A61B 2090/3925; A61B 2090/3966;
(Continued)

(56) References Cited

U.S. PATENT DOCUMENTS 4,341,218 A 7/1982 U
5,137,515 A 8/1992 Hogan
(Continued)

FOREIGN PATENT DOCUMENTS

CN 102202718 B 9/2011
JP S55-133265 A 10/1980
(Continued)

OTHER PUBLICATIONS

Chinese Office Action for Appln. No. 202080102387.5 mailed Sep. 9, 2024, 19 pages.
(Continued)

*Primary Examiner* — Serkan Akar
*Assistant Examiner* — Tommy T Ly
(74) *Attorney, Agent, or Firm* — DINSMORE & SHOHL LLP

(57) ABSTRACT

A breast biopsy marker includes a catheter shaft and a bioabsorbable balloon. The catheter shaft has a lumen, a proximal tube portion, and a distal tube portion. The proximal tube portion is joined to the distal tube portion by a frangible link. The distal tube portion has a one-way valve located in the lumen. The bioabsorbable balloon is fixedly connected to the distal tube portion to define a balloon assembly. The bioabsorbable balloon is configured for fluid communication with the lumen of the catheter shaft at a location distal to the one-way valve of the distal tube portion of the catheter shaft. The balloon assembly is configured to be separated from the proximal tube portion of the catheter shaft by breaking the frangible link.

20 Claims, 2 Drawing Sheets

(52) U.S. Cl.
CPC ................. *A61B 2090/3925* (2016.02); *A61B 2090/3966* (2016.02); *A61B 2090/3995* (2016.02); *A61M 2025/1079* (2013.01)

(58) Field of Classification Search
CPC .. A61B 2090/3995; A61B 2017/00557; A61B 2017/00632; A61B 2017/22062; A61B 2017/00004; A61B 2017/00796; A61B 2090/037; A61B 2090/3933; A61B 2090/3987; A61M 2025/1079; A61F 2210/0004; A61F 2250/0003; A61F 2250/0071; A61F 2250/0098; A61F 2/12
See application file for complete search history.

(56) References Cited

U.S. PATENT DOCUMENTS

| | | | | |
|---|---|---|---|---|
| 5,301,682 | A | 4/1994 | Debbas | |
| 5,383,889 | A | 1/1995 | Warner et al. | |
| 5,861,005 | A * | 1/1999 | Kontos | A61B 17/0682 606/139 |
| 6,161,034 | A | 12/2000 | Burbank et al. | |
| 6,214,045 | B1 | 4/2001 | Corbitt et al. | |
| 6,272,372 | B1 | 8/2001 | Fisher | |
| 6,356,782 | B1 | 3/2002 | Sirimanne et al. | |
| 6,371,904 | B1 | 4/2002 | Sirimanne et al. | |
| 6,427,081 | B1 | 7/2002 | Burbank et al. | |
| 6,862,470 | B2 | 3/2005 | Burbank et al. | |
| 6,997,885 | B2 | 2/2006 | Lubock et al. | |
| 7,534,452 | B2 | 5/2009 | Chernomorsky et al. | |
| 7,637,948 | B2 | 12/2009 | Corbitt, Jr. | |
| 7,871,438 | B2 | 1/2011 | Corbitt, Jr. | |
| 7,963,928 | B2 | 6/2011 | Krause | |
| 8,668,737 | B2 | 3/2014 | Corbitt, Jr. | |
| 9,456,878 | B2 | 10/2016 | Macfarlane et al. | |
| 9,669,113 | B1 | 6/2017 | Sirimanne et al. | |
| 10,045,832 | B2 | 8/2018 | Burbank et al. | |
| 2005/0192616 | A1 | 9/2005 | Callister et al. | |
| 2005/0234336 | A1* | 10/2005 | Beckman | A61B 90/39 600/431 |
| 2006/0079727 | A1 | 4/2006 | Chernomorsky et al. | |
| 2009/0131825 | A1* | 5/2009 | Burbank | A61M 37/0069 600/567 |
| 2009/0149746 | A1 | 6/2009 | Chernomorsky et al. | |
| 2009/0299401 | A1* | 12/2009 | Tilson | A61M 25/1029 606/192 |
| 2012/0078086 | A1* | 3/2012 | Hoffa | A61B 10/0275 600/567 |
| 2012/0330340 | A1* | 12/2012 | Shohat | A61B 8/445 606/190 |
| 2016/0100843 | A1 | 4/2016 | Sideris | |
| 2016/0228126 | A1* | 8/2016 | Squire | A61B 17/12109 |
| 2019/0008606 | A1* | 1/2019 | Ahn | A61K 49/1803 |
| 2019/0076274 | A1* | 3/2019 | Hingston | A61L 31/14 |
| 2020/0261067 | A1* | 8/2020 | Small | A61B 10/0266 |
| 2021/0128140 | A1* | 5/2021 | Wales | A61B 17/0487 |
| 2022/0071732 | A1* | 3/2022 | Rebellino | A61B 17/3468 |

FOREIGN PATENT DOCUMENTS

| | | | |
|---|---|---|---|
| JP | 2006333888 | A | 12/2006 |
| WO | 00/045854 | A2 | 8/2000 |
| WO | 2008042819 | A2 | 4/2008 |
| WO | 2018136621 | A1 | 7/2018 |

OTHER PUBLICATIONS

International Search Report and Written Opinion dated Mar. 19, 2021, in International Application No. PCT/US2020/039300.

Japanese Office Action for Appln. No. 2022-580103 mailed Dec. 3, 2024, 11 pages.

* cited by examiner

BREAST BIOPSY MARKER AND SYSTEM

CROSS-REFERENCE TO RELATED APPLICATIONS

This application is a U.S. National Phase of International Application No. PCT/US2020/039300, entitled "Breast Biopsy Marker And System" and filed Jun. 24, 2020, which is incorporated herein by reference in its entirety.

TECHNICAL FIELD

The present invention relates to a breast biopsy apparatus, and, more particularly, to a breast biopsy marker and system.

BACKGROUND ART

Biopsy diagnostics and treatment often include the performing of a biopsy, such as a breast biopsy, in which a specimen or sample of tissue is removed from the patient at the biopsy site for pathological examination, tests and analysis. Obtaining a tissue sample by biopsy and the subsequent examination are typically employed in the diagnosis of cancers and other malignant tumors, or to confirm that a suspected lesion or tumor is not malignant. For example, a breast biopsy may be taken where a suspicious lump or swelling is noticed in a breast. Examination of tissue samples taken by the biopsy is of particular significance in the diagnosis and treatment of breast cancer.

After the biopsy is performed, it may take several days or weeks before the results of the examination of the sample are obtained, and still longer before an appropriate treatment decision is reached. If the decision involves surgery, it is important for the surgeon to find the location (biopsy site) in the breast from where the tumor tissue has been taken in the biopsy procedure, so that the entire tumor and possibly surrounding healthy tissue can be removed.

Various types of biopsy site markers are available, including visible markers applied externally to the patient's skin, radiographically (X-ray)-detectable tissue markers such as clips and staples, and ultrasound-detectable markers, to aid the physician in locating the biopsy site. However, such markers are not effective in filling the biopsy cavity for also providing a cosmetic benefit.

What is needed in the art is a breast biopsy marker and system that helps the physician in re-acquiring the location of the biopsy site, aids in patient healing, and/or provides a cosmetic benefit to the patient.

SUMMARY OF INVENTION

The present invention provides a breast biopsy marker and system that helps the physician in re-acquiring the location of the biopsy site, aids in patient healing, and/or provides a cosmetic benefit to the patient.

The invention, in one form, is directed to a breast biopsy marker that includes a catheter shaft and a bioabsorbable balloon. The catheter shaft has a lumen, a proximal tube portion, and a distal tube portion. The proximal tube portion is joined to the distal tube portion by a frangible link. The distal tube portion has a one-way valve located in the lumen. The bioabsorbable balloon is fixedly connected to the distal tube portion to define a balloon assembly. The bioabsorbable balloon is configured for fluid communication with the lumen of the catheter shaft at a location distal to the one-way valve of the distal tube portion of the catheter shaft. The balloon assembly is configured to be separated from the proximal tube portion of the catheter shaft by breaking the frangible link.

The invention in another form is directed to a breast biopsy marker system that includes a catheter shaft, a bioabsorbable balloon, a syringe, and an elongate stylet. The catheter shaft has a lumen, a proximal tube portion, and a distal tube portion. The proximal tube portion is joined to the distal tube portion by a frangible link. The distal tube portion has a one-way valve located in the lumen. The bioabsorbable balloon is fixedly connected to the distal tube portion to define a balloon assembly. The bioabsorbable balloon is configured for fluid communication with the lumen of the catheter shaft at a location distal to the one-way valve of the distal tube portion of the catheter shaft. The syringe is configured to carry a gel material. The syringe has an injection port connectable to the proximal tube portion of the catheter shaft. The syringe is configured to deliver the gel material through the lumen of the catheter shaft to the bioabsorbable balloon. The elongate stylet is configured for insertion into the lumen of the catheter shaft to break the frangible link of the catheter shaft following inflation of the bioabsorbable balloon with the gel material delivered by the syringe, so as to separate the proximal tube portion of the catheter shaft from the balloon assembly.

An advantage of the present invention is that the breast biopsy marker helps the physician in re-acquiring the location of the biopsy site and provides a cosmetic benefit to the patient.

Another advantage of the present invention is that the breast biopsy marker may aid in healing by providing internal applied pressure at the biopsy site and a biodegradable scaffold/support for the tissue to heal around.

Another advantage of the present invention is that the breast biopsy marker may provide a cosmetic benefit to the patient by inflating the biopsy cavity.

Another advantage is that the breast biopsy marker is that it may be immediately placed and inflated following the biopsy through the existing biopsy tract, without the need for a new or future incision or puncture for marker placement.

Another advantage is that materials for the breast biopsy marker may be selected so as to provide both short term and long term imaging visibility in multiple imaging modalities.

BRIEF DESCRIPTION OF DRAWINGS

The above-mentioned and other features and advantages of this invention, and the manner of attaining them, will become more apparent and the invention will be better understood by reference to the following description of an embodiments of the invention taken in conjunction with the accompanying drawings, wherein.

Corresponding reference characters indicate corresponding parts throughout the several views. The exemplifications set out herein illustrate at least one embodiment of the invention, and such exemplifications are not to be construed as limiting the scope of the invention in any manner.

DESCRIPTION OF EMBODIMENTS

Figure 1:
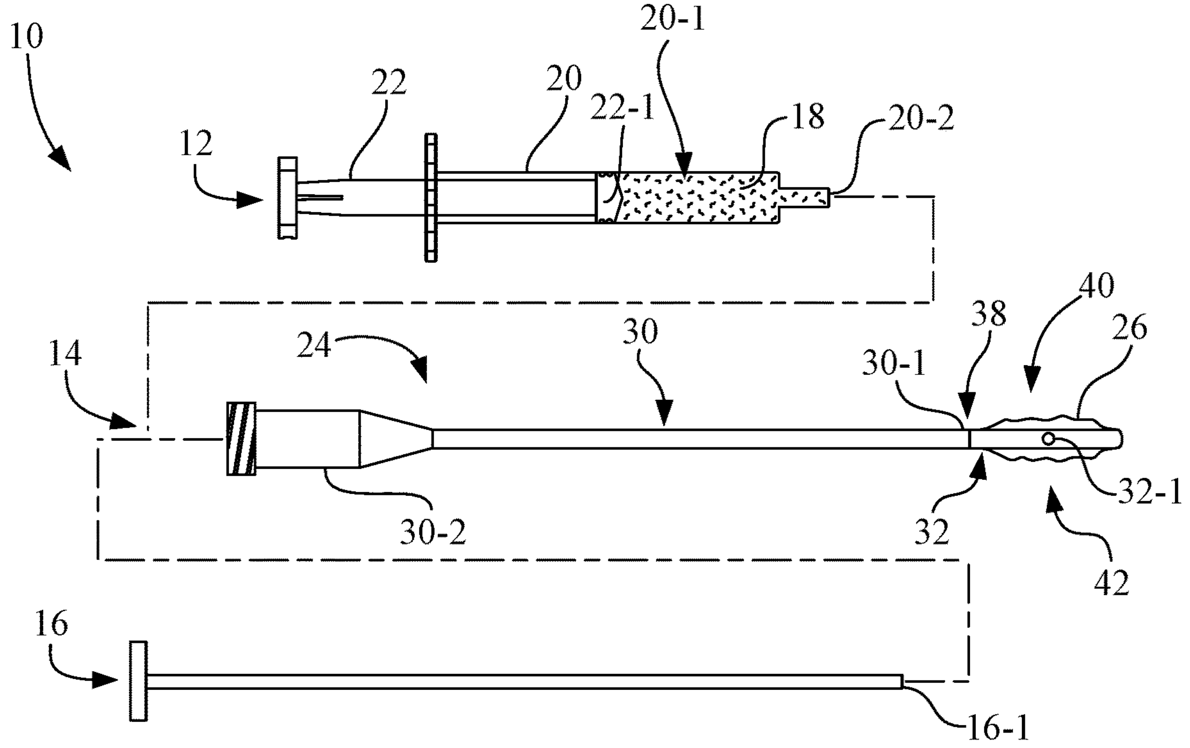
FIG. 1 is an exploded view of the breast biopsy marker system in accordance with an aspect of the present invention, with the bioabsorbable balloon of the marker catheter being in a deflated state.

Referring now to the drawings, and more particularly to FIG. 1, there is shown a breast biopsy marker system 10 which generally includes a syringe 12, a marker catheter 14, and an elongate stylet 16.

Syringe 12 is configured to carry a gel material 18, such as a hydrogel. Syringe 12 may include, for example, a cylinder 20 having a chamber 20-1 and a plunger 22 having a piston 22-1 disposed in chamber 20-1 proximal to gel material 18. Cylinder 20 of syringe 12 has an injection port 20-2 that is connectable to marker catheter 14. Syringe 12 configured to deliver gel material 18 into marker catheter 14, as will be described in more detail below.

While in the present embodiment syringe 12 is shown as having a single chamber 20-1 that is configured to carry a pre-prepared gel as gel material 18, those skilled in the art will recognize that syringe 12 may be modified to have multiple (e.g., dual) chambers that contain the constituent component parts for forming a gel after the constituent component parts are combined. Accordingly, as used herein, the term "gel material" is intended to be interpreted broadly to include both pre-prepared gels and the constituent component parts which when combined, e.g., mixed, form a gel.

Figure 2:
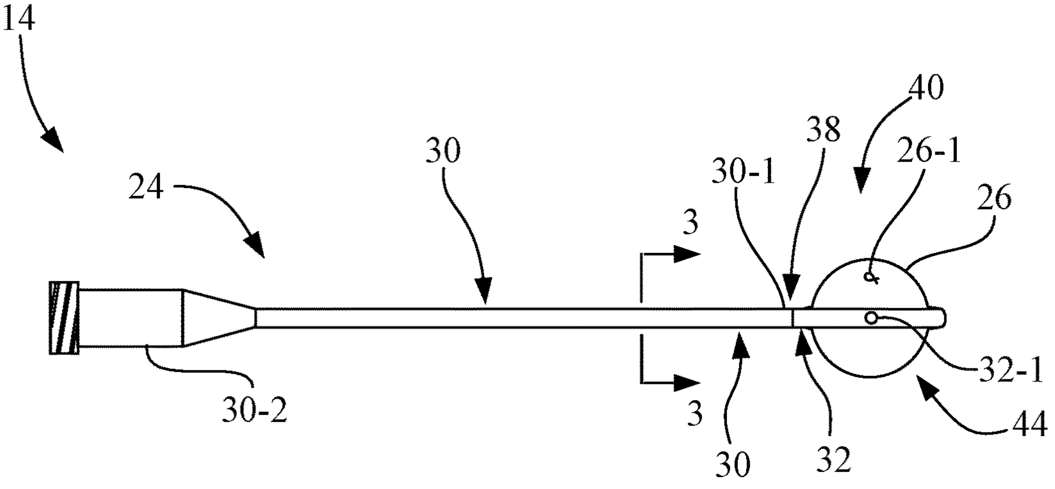
FIG. 2 is a side view of the marker catheter of FIG. 1, with the bioabsorbable balloon being in an inflated state.
Figure 3:
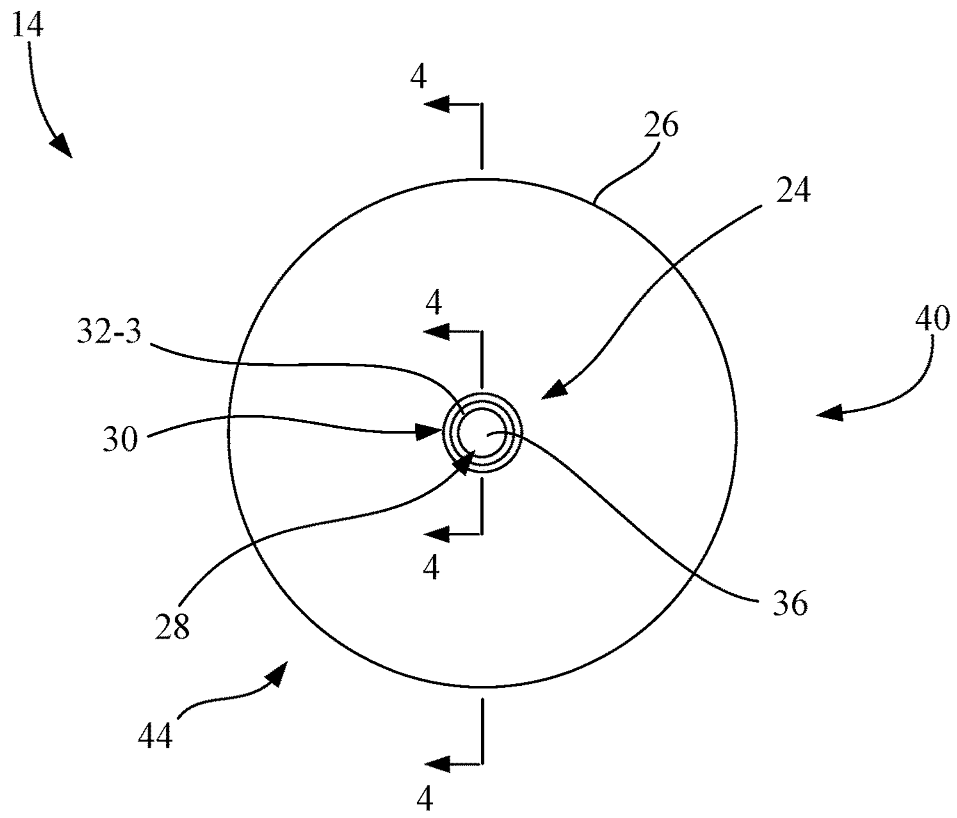
FIG. 3 is an enlarged section view of the marker catheter of FIG. 2, taken along line 3-3 of FIG. 2.

Referring also to FIGS. 2 and 3, marker catheter 14 includes a catheter shaft 24 and a bioabsorbable balloon 26. Bioabsorbable balloon 26 may be made from a polymer, such as for example, a poly (glycolide-co-lactide) (PGLA) material, and optionally, may include at least one radiopaque and ultrasonically visible marker element 26-1, e.g., a titanium ribbon, that is imbedded in the PGLA material, so as to provide both short term and long term imaging visibility in multiple imaging modalities.

Catheter shaft 24 includes a lumen 28, a proximal tube portion 30, and a distal tube portion 32. Proximal tube portion 30 may be made, for example, of a non-biodegradable material. Distal tube portion 32 may be made, for example, of a non-biodegradable material and optionally may include a non-biodegradable component, e.g., etching, that provides permanent ultrasound visibility, thus yielding long term imaging visibility under ultrasound. The non-biodegradable material of proximal tube portion 30 may be, for example, a PEBAX® brand polymer (PEBAX is a registered trademark of the Arkema France Corporation France). The non-biodegradable material and component of distal tube portion 32 may be, for example, polyvinyl alcohol.

In accordance with an aspect of the present invention, proximal tube portion 30 is joined to distal tube portion 32 by a frangible link 34. Distal tube portion 32 includes a one-way valve 36, e.g., a check valve, such as a pivotable flap, that is located in lumen 28, and a side wall orifice 32-1 in fluid communication with lumen 28. Injection port 20-2 of syringe 12 is releasably connectable, e.g., by a Luer or friction connection, to proximal tube portion 30 of catheter shaft 24 to facilitate delivery of gel material 18 into lumen 28 of catheter shaft 24.

Figure 4:
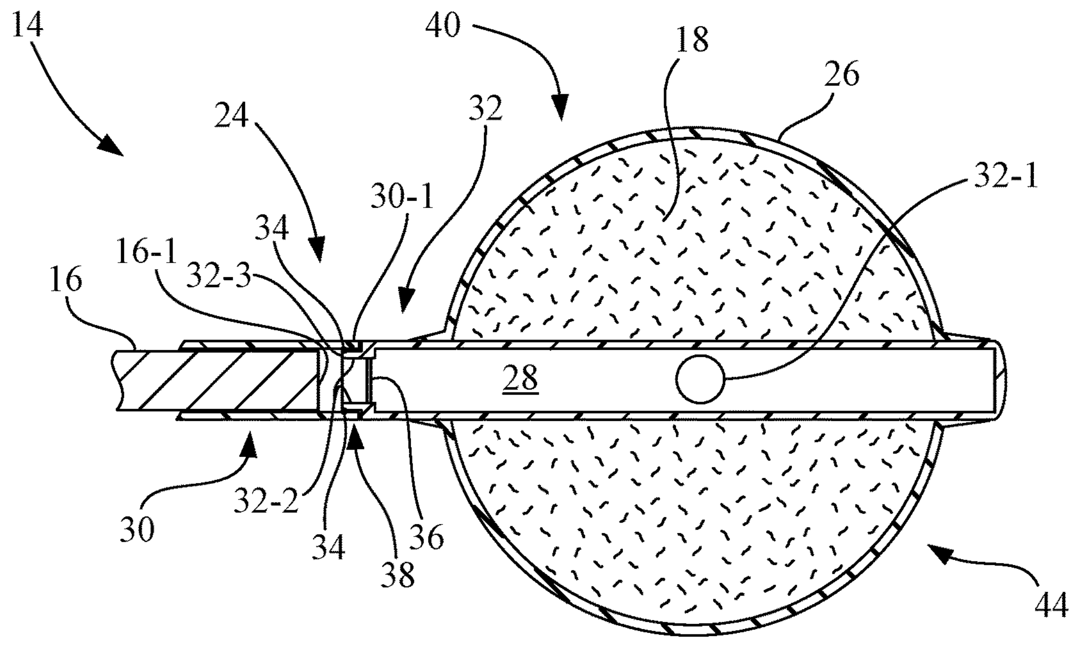
FIG. 4 is a section view of the marker catheter of FIG. 3, taken along line 4-4-4-4 of FIG. 3.

In the present embodiment, with reference to FIGS. 2-4, proximal tube portion 30 has a first end portion 30-1 and a hub portion 30-2, and distal tube portion 32 has a second end portion 32-2 having a proximal end surface 32-3. Second end portion 32-2 of distal tube portion 32 is positioned inside first end portion 30-1 of proximal tube portion 30, such that first end portion 30-1 of proximal tube portion 30 radially overlaps second end portion 32-2 of distal tube portion 32 to define an overlap region 38. As such, proximal end surface 32-3 of distal tube portion 32 is proximally exposed in lumen 28 of catheter shaft 24.

Frangible link 34 joins proximal tube portion 30 to distal tube portion 32 and may be located at overlap region 38 between proximal tube portion 30 and distal tube portion 32. For example, frangible link 34 may join proximal tube portion 30 to distal tube portion 32 by a breakable connection that is connected to each of proximal end surface 32-3 of second end portion 32-2 of distal tube portion 32 and proximal tube portion 30. In the present embodiment, for example, frangible link 34 is a spot weld.

Referring to FIGS. 1-4, bioabsorbable balloon 26 is fixedly connected, e.g., via adhesive, laser welding, or shrink tubing, to distal tube portion 32 to define a balloon assembly 40. Syringe 12 is configured to deliver gel material 18 through lumen 28 of catheter shaft 24 to bioabsorbable balloon 26. Bioabsorbable balloon 26 has a deflated state 42 (see FIG. 1) and an inflated state 44 (see FIGS. 2-4). In the deflated state 42, balloon assembly 40 of marker catheter 14 may be inserted into a biopsy cavity, e.g., a breast biopsy cavity, of a patient.

Referring particularly to FIGS. 2-4, when injection port 20-2 of syringe 12 is connected to proximal tube portion 30 of catheter shaft 24, then bioabsorbable balloon 26 of balloon assembly 40 is coupled in fluid communication with syringe 12 via lumen 28 of catheter shaft 24. Accordingly, upon actuation of syringe 12, e.g., by depressing plunger 22, gel material 18 is delivered into bioabsorbable balloon 26 so as to inflate bioabsorbable balloon 26. In the present embodiment, bioabsorbable balloon 26 is configured for fluid communication with lumen 28 of catheter shaft 24 at a location distal to one-way valve 36 of distal tube portion 32 of catheter shaft 24. Accordingly, gel material 18 may be inserted into bioabsorbable balloon 26 through one-way valve 36 and side wall orifice 32-1 of distal tube portion 32 of catheter shaft 24 to effect the inflated state 44 of bioabsorbable balloon 26, wherein one-way valve 36 is configured to prevent a return from the inflated state 44 to the deflated state 42. In other words, as bioabsorbable balloon 26 of balloon assembly 40 is being inflated with gel material 18, then one-way valve 36 of distal tube portion 32 of catheter shaft 24 of balloon assembly 40 prevents a backflow of gel material 18, such that bioabsorbable balloon 26 is retained in a permanent inflated state 44.

Elongate stylet 16 is configured, e.g., as an elongate tube or rod, for insertion into lumen 28 of catheter shaft 24 to break frangible link 34 so as to separate proximal tube portion 30 of catheter shaft 24 from balloon assembly 40. In particular, elongate stylet 16 is configured for insertion into lumen 28 of catheter shaft 24 to break frangible link 34 of catheter shaft 24 following inflation of bioabsorbable balloon 26 with gel material 18 delivered by the syringe 12, so as to separate proximal tube portion 30 of catheter shaft 24 from balloon assembly 40.

For example, elongate stylet 16 is inserted into, and is advanced in, lumen 28 in proximal tube portion 30 of catheter shaft 24 such that distal end 16-1 of elongate stylet 16 engages proximal end surface 32-3 of second end portion 32-2 of distal tube portion 32 and/or frangible link 34. Elongate stylet 16 then may be further advanced, e.g., e.g., 0.5 to 2 millimeters, with a sufficient force so as to break frangible link 34, thereby separating proximal tube portion 30 from balloon assembly 40. After frangible link 34 is broken, then proximal tube portion 30 may be withdrawn from the patient while balloon assembly 40, in the inflated state 44, remains in the biopsy cavity of the patient.

Gel material 18 contained in bioabsorbable balloon 26 will be degraded in the patient over 12 to 18 months as bioabsorbable balloon 26 is resorbed. In some implementations, for example, gel material 18 may be, for example, a polyethylene glycol (PEG) based hydrogel, sodium hyaluronate (hyaluronic acid), or an aloe vera gel. Sodium hyaluronate encompasses wound-healing benefits and may be modified to exhibit thermoset properties. Thermoset properties of the gel material 18 may be desirable because it allows the material to be in a liquid state for inflation and then thicken to a gel-like consistency once it reaches body temperature. This allows for the ability to apply a minimal amount of pressure to inflate bioabsorbable balloon 26. In some implementations, PEG may be a desirable material due to its long-term, predictable degradation timeline and its ultrasound visibility properties. Aloe vera also encompasses wound-healing benefits, but does not allow for thermoset functionality.

The following items also relate to the invention.

In one embodiment, the invention relates to a breast biopsy marker (assembly) that includes a catheter shaft and a bioabsorbable balloon. The catheter shaft has a lumen, a proximal tube portion, and a distal tube portion. The proximal tube portion is joined to the distal tube portion by a frangible (breakable) link and/or a link which is structured to break, separate and/or disjoin. The distal tube portion may have a one-way valve located in the lumen. The bioabsorbable balloon is (fixedly) connected to the distal tube portion to define a balloon assembly. The bioabsorbable balloon may be configured for fluid communication with the lumen of the catheter shaft at a location distal to the one-way valve of the distal tube portion of the catheter shaft. The balloon assembly and/or the breast biopsy marker (assembly) is configured such that the balloon assembly can be separated from the proximal tube portion of the catheter shaft by breaking the frangible link.

In any of the embodiments, the bioabsorbable balloon may have a deflated state and an inflated state. Alternatively or additionally, a gel material may be configured to be inserted into the bioabsorbable balloon through the one-way valve of the distal tube portion of the catheter shaft to effect the inflated state of the bioabsorbable balloon.

In any of the embodiments, the proximal tube portion of the catheter shaft has a first end portion. The distal tube portion has a second end portion that has a proximal end surface. The second end portion of the distal tube portion may be positioned inside the first end portion of the proximal tube portion such that the first end portion of the proximal tube portion radially overlaps the second end portion of the distal tube portion to define an overlap region, and such that the proximal end surface of the distal tube portion may be proximally exposed in the lumen of the catheter shaft.

In the embodiment of paragraph 0037, the frangible link that joins the proximal tube portion to the distal tube portion may be located at the overlap region.

In the embodiment of paragraph 0037, the frangible link that joins the proximal tube portion to the distal tube portion may be connected to each of the proximal end surface of the second end portion of the distal tube portion and the proximal tube portion.

In any of the embodiments, the frangible link may be a spot weld.

Optionally, for use with any of the embodiments, an elongate stylet may be configured for insertion into the lumen of the catheter shaft to break the frangible link to separate the proximal tube portion of the catheter shaft from the balloon assembly.

In any of the embodiments, the bioabsorbable balloon may be made of a PGLA material, and optionally further comprising at least one radiopaque and/or ultrasonically visible marker element imbedded in the PGLA material.

In any of the embodiments, the proximal tube portion may be made with a non-biodegradable material and/or the distal tube portion may include a non-biodegradable component configured to provide permanent ultrasound visibility.

In the embodiment of paragraph 0043, the non-biodegradable material of the proximal tube portion may be a PEBAX brand polymer and/or the non-biodegradable component of the distal tube portion may be polyvinyl alcohol.

In another embodiment, the invention relates to a breast biopsy marker system. The system may include a catheter shaft, a bioabsorbable balloon, a syringe, and an elongate stylet. The catheter shaft may be the catheter shaft of paragraph and/or may have a lumen, a proximal tube portion, and a distal tube portion. The proximal tube portion is joined to the distal tube portion by a frangible link. The distal tube portion may have a one-way valve located in the lumen. The bioabsorbable balloon may be the bioabsorbable balloon of paragraph and/or may be (fixedly) connected to the distal tube portion to define a balloon assembly. The bioabsorbable balloon may be configured for fluid communication with the lumen of the catheter shaft at a location distal to the one-way valve of the distal tube portion of the catheter shaft. The syringe may be configured to carry a gel material. The syringe may have an injection port that may be connected, or is connectable, to the proximal tube portion of the catheter shaft. The syringe may be configured to deliver the gel material through the lumen of the catheter shaft to the bioabsorbable balloon. The elongate stylet may be configured for insertion into the lumen of the catheter shaft to break the frangible link of the catheter shaft following inflation of the bioabsorbable balloon with the gel material delivered by the syringe, so as to separate the proximal tube portion of the catheter shaft from the balloon assembly. The system may be configured such that the elongate stylet can break the frangible link of the catheter shaft following inflation of the bioabsorbable balloon with the gel material delivered by the syringe, so as to separate the proximal tube portion of the catheter shaft from the balloon assembly.

In any of the system embodiments, the bioabsorbable balloon may have a deflated state and an inflated state. Alternatively or additionally, the gel material may be configured to be inserted into the bioabsorbable balloon through the one-way valve of the distal tube portion of the catheter shaft to effect the inflated state of the bioabsorbable balloon. The one-way valve may be configured to prevent a return from the inflated state to the deflated state.

In any of the system embodiments, the proximal tube portion of the catheter shaft has a first end portion. The distal tube portion may have a second end portion having a proximal end surface. The second end portion of the distal tube portion may be positioned inside the first end portion of the proximal tube portion such that the first end portion of the proximal tube portion radially overlaps the second end portion of the distal tube portion to define an overlap region, and such that the proximal end surface of the distal tube portion may be proximally exposed in the lumen of the catheter shaft.

In the system embodiment of paragraph 0047, the frangible link that joins the proximal tube portion to the distal tube portion may be located at the overlap region between the proximal tube portion and the distal tube portion.

In the system embodiment of paragraph 0047, the frangible link that joins the proximal tube portion to the distal tube portion may be connected to each of the proximal end surface of the second end portion of the distal tube portion and the proximal tube portion.

In any of the system embodiments, the frangible link may be a spot weld.

In any of the system embodiments, the elongate stylet may be configured as an elongate tube or rod that may be inserted into the lumen of the catheter shaft to break the frangible link to separate the proximal tube portion of the catheter shaft from the balloon assembly.

In any of the system embodiments, the bioabsorbable balloon may be made of a PGLA material and may optionally further comprise at least one radiopaque and/or ultrasonically visible marker element that may be imbedded in the PGLA material.

In any of the system embodiments, the proximal tube portion may be made with a non-biodegradable material and/or the distal tube portion may include a non-biodegradable component configured to provide permanent ultrasound visibility.

In the system embodiment of paragraph 0053, the non-biodegradable material of the proximal tube portion may be a PEBAX brand polymer and/or the non-biodegradable component of the distal tube portion may be polyvinyl alcohol.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A breast biopsy marker delivery device, comprising:
- a catheter shaft having:
  - a lumen,
  - a proximal tube portion having a first end portion,
  - a distal tube portion joined to the proximal tube portion by a frangible link, the distal tube portion having a second end portion with a proximal end surface, the second end portion of the distal tube portion being positioned inside the first end portion of the proximal tube portion such that the first end portion of the proximal tube portion radially overlaps the second end portion of the distal tube portion to define an overlap region, and such that the proximal end surface of the distal tube portion is proximally exposed in the lumen of the catheter shaft, and
  - a one-way valve located in the lumen and inside the second end portion of the distal tube portion, the one-way valve being positioned outside the overlap region and within a reduced diameter region of the second end portion; and
- a bioabsorbable balloon fixedly connected to the distal tube portion to define a balloon assembly, the bioabsorbable balloon configured for fluid communication with the lumen of the catheter shaft at a location distal to the one-way valve of the distal tube portion of the catheter shaft, the balloon assembly configured to be separated from the proximal tube portion of the catheter shaft by breaking the frangible link, wherein the bioabsorbable balloon and the distal tube portion define a breast biopsy marker shaped, in the inflated state to apply pressure to and fill a breast biopsy site after a breast biopsy procedure, wherein the breast biopsy marker is radiopaque, ultrasonically visible, or both;
- wherein the bioabsorbable balloon has a circular cross section in an axial plane when in its inflated state.

2. The breast biopsy marker delivery device according to claim 1, the bioabsorbable balloon having a deflated state and an inflated state, and comprising a gel material configured to be inserted into the bioabsorbable balloon through the one-way valve of the distal tube portion of the catheter shaft to effect the inflated state of the bioabsorbable balloon.

3. The breast biopsy marker delivery device according to claim 1, wherein the frangible link that joins the proximal tube portion to the distal tube portion is located at the overlap region.

4. The breast biopsy marker delivery device according to claim 1, wherein the frangible link that joins the proximal tube portion to the distal tube portion is connected to each of the proximal end surface of the second end portion of the distal tube portion and the proximal tube portion.

5. The breast biopsy marker delivery device of claim 1, wherein the frangible link is a spot weld.

6. The breast biopsy marker delivery device of claim 1, comprising an elongate stylet configured for insertion into the lumen of the catheter shaft to break the frangible link to separate the proximal tube portion of the catheter shaft from the balloon assembly.

7. The breast biopsy marker delivery device of claim 1, wherein the bioabsorbable balloon is made of a poly (glycolide-co-lactide) (PGLA material), and further comprising at least one radiopaque and ultrasonically visible marker element imbedded in a wall of the balloon.

8. The breast biopsy marker delivery device of claim 1, wherein the proximal tube portion is made with a non-biodegradable material and the distal tube portion includes a non-biodegradable component configured to provide permanent ultrasound visibility and wherein the non-biodegradable component of the distal tube portion is formed from polyvinyl alcohol.

9. The breast biopsy marker delivery device of claim 1, wherein the bioabsorbable balloon is fixedly connected to the distal tube portion at a proximal end of the distal tube portion and a distal end of the distal tube portion.

10. The breast biopsy marker delivery device of claim 1, wherein the proximal end surface includes an opening through which the lumen extends from the proximal tube portion into the distal tube portion.

11. The breast biopsy marker delivery device of claim 10, wherein the distal tube portion includes a side wall orifice placing the lumen in fluid communication with an interior of the balloon, the side wall orifice extending perpendicularly relative to the opening in the proximal end surface, the side wall orifice being distal to the one-way valve.

12. A breast biopsy marker system, comprising:
- a catheter shaft having:
  - a lumen,
  - a proximal tube portion having a first end portion,
  - a distal tube portion joined to the distal tube portion by a frangible link, the distal tube portion having a second end portion with a proximal end surface, the second end portion of the distal tube portion being positioned inside the first end portion of the proximal tube portion such that the first end portion of the proximal tube portion radially overlaps the second end portion of the distal tube portion to define an overlap region, and such that the proximal end surface of the distal tube portion is proximally exposed in the lumen of the catheter shaft, and a one-way valve located in the lumen and inside the second end portion of the distal tube portion, the one-way valve being positioned outside the overlap region and within a reduced diameter region of the second end portion;

a bioabsorbable balloon fixedly connected to the distal tube portion to define a balloon assembly, the bioabsorbable balloon configured for fluid communication with the lumen of the catheter shaft at a location distal to the one-way valve of the distal tube portion of the catheter shaft;

a syringe configured to carry a gel material, the syringe having an injection port connectable to the proximal tube portion of the catheter shaft, the syringe configured to deliver the gel material through the lumen of the catheter shaft to the bioabsorbable balloon; and an elongate stylet configured for insertion into the lumen of the catheter shaft to break the frangible link of the catheter shaft following inflation of the bioabsorbable balloon with the gel material delivered by the syringe, so as to separate the proximal tube portion of the catheter shaft from the balloon assembly, wherein the bioabsorbable balloon and the distal tube portion define a breast biopsy marker shaped, in the inflated state to apply pressure to and fill a breast biopsy site after a breast biopsy procedure, wherein the breast biopsy marker is radiopaque, ultrasonically visible, or both;

wherein the bioabsorbable balloon has a circular cross section in an axial plane when in its inflated state.

13. The breast biopsy marker system according to claim 12, wherein the bioabsorbable balloon has a deflated state and an inflated state, and wherein the gel material is configured to be inserted into the bioabsorbable balloon through the one-way valve of the distal tube portion of the catheter shaft to effect the inflated state of the bioabsorbable balloon, the one-way valve configured to prevent a return from the inflated state to the deflated state.

14. The breast biopsy marker system according to claim 12, wherein the frangible link that joins the proximal tube portion to the distal tube portion is located at the overlap region between the proximal tube portion and the distal tube portion.

15. The breast biopsy marker system according to claim 12, wherein the frangible link that joins the proximal tube portion to the distal tube portion is connected to each of the proximal end surface of the second end portion of the distal tube portion and the proximal tube portion.

16. The breast biopsy marker system of claim 12, wherein the frangible link is a spot weld.

17. The breast biopsy marker system of claim 12, wherein the elongate stylet is configured as an elongate tube or rod for insertion into the lumen of the catheter shaft to break the frangible link to separate the proximal tube portion of the catheter shaft from the balloon assembly.

18. The breast biopsy marker system of claim 12, wherein the bioabsorbable balloon is made of a poly (glycolide-co-lactide) (PGLA) material, and further comprising at least one radiopaque and ultrasonically visible marker element imbedded in a wall of the balloon.

19. The breast biopsy marker system of claim 12, wherein the proximal tube portion is made with a non-biodegradable material and the distal tube portion includes a non-biodegradable component configured to provide permanent ultrasound visibility, and wherein the non-biodegradable component of the distal tube portion is formed from polyvinyl alcohol.

20. The breast biopsy marker delivery device of claim 12, wherein the lumen comprises a single lumen such that the catheter shaft has only the single lumen extending therethrough, each of the gel material and the elongate stylet being passable at least partially through the single lumen.

* * * * *